United States Patent [19]

Curstedt et al.

[11] Patent Number: 5,223,481

[45] Date of Patent: Jun. 29, 1993

[54] BIOLOGICALLY ACTIVE LIPOPROTEIN AND ITS USE

[75] Inventors: Tore Curstedt, Sollentuna; Hans Jörnvall, Sundbyberg; Björn Löwenadler, Täby; Bengt Robertsson, Stockholm, all of Sweden

[73] Assignee: KabiGen AB, Stockholm, Sweden

[21] Appl. No.: 423,346

[22] Filed: Oct. 18, 1989

[30] Foreign Application Priority Data

Oct. 18, 1988 [SE] Sweden ............................ 8803713

[51] Int. Cl.$^5$ ..................... C07K 15/16; C07K 7/10; A61K 37/00
[52] U.S. Cl. ..................................... 514/12; 514/14; 514/17; 514/21; 530/359; 530/324
[58] Field of Search ..................... 530/410, 324, 359; 514/12, 21, 14, 17

[56] References Cited

U.S. PATENT DOCUMENTS

| | | | |
|---|---|---|---|
| 4,234,475 | 11/1980 | Sokol | 530/327 |
| 4,406,833 | 9/1983 | Boehme et al. | 530/410 |
| 4,659,805 | 4/1987 | Schiling, Jr. et al. | 530/350 |
| 4,861,756 | 8/1990 | Jackson | 514/11 |
| 4,882,422 | 11/1989 | Taeusch et al. | 530/350 |
| 4,918,161 | 4/1990 | Steinbrink et al. | 530/300 |
| 4,933,280 | 6/1990 | Schilling, Jr. et al. | 435/69.1 |
| 5,013,720 | 5/1991 | Whitsett | 514/12 |

FOREIGN PATENT DOCUMENTS 0286011 10/1988 European Pat. Off.

OTHER PUBLICATIONS

Curstedt, et al., *Eur. J. Biochem.*, 168: 255-262 (1987).
Curstedt, et al., *Proc. Natl. Acad. Sci.*, 87: 2985-2989, (Apr. 1990).
Smith, et al., *Pediatric Res.*, 23(5): 484-490, 1988.
Goerke, J. (1974) Biochim. Biophys. Acta 374, 241-261.
King, R. J., Klass; D. J., Gikas, E. G. and Clements, J. A. (1973) Am. J. Physiol. 224., 788-795.
van Golde, L. M. G., Batenburg, J. J. and Robertson, B. (1987) Physiol. Rev., in press.
Benson, B., Hawgood, S., Shilling, J., Clements, J., Damm, D., Cordell B. and White, R. T. (1985) Proc. Natl. Acad. Sci. USA 82, 6379-6383.
White, R. T., Damm; D., Miller, J., Spratt, K., Shilling, J., Hawgood, S., Benson, B. and Cordell, B. (1985) Nature 317, 361-363.
Floros, I., Steinbrink, R., Jacobs, K., Phelps, D., Kriz, R., Recny, M., Sultzmann, L., Jones, S., Taeusch, H. W., Frank, H. A. and Fritsch, E. F. (1986) J. Biol. Chem. 261, 9029-9033.
Benson, B. J., Williams, M. S., Sueishi, K., Goerke, J. and Sargeant, T. (1984) Biochim. Biophys. Acta 793, 18-27.
King, R. J. and MacBeath, M. C. (1979) Biochim, Biophys. Acta 557, 86-101.
Whitsett, J. A., Ohning, B. L., Ross, G., Meuth, J., Weaver, T., Holm, B. A., Shapiro, D. L. and Notter, R. H. (1986) Pediatr. Res. 20, 460-467.
Metcalfe, I. L., Enhorning, G. and Possmayer, F. (1980) J. Appl. Physiol. 49, 34-41.
Berggren, P., Curstedt, T., Grossman, G., Nilsson, R. and Robertson, B. (1985) Exp. Lung Res. 8, 29-51.
Phizackerley, P. J. R., Town, M.-H. and Newman, G. E. (1979) Biochem. J. 1983; 731-736.
Katyal, S. L. and Singh, G. (1979) Lab. Invest. 40, 562-567.

(List continued on next page.)

Primary Examiner—Howard E. Schain
Attorney, Agent, or Firm—Burns, Doane, Swecker & Mathis

[57] ABSTRACT

A lipoprotein possessing pulmonary surfactant activity comprising an alveolar polypeptide or protein and, covalently bound thereto, one or two fatty acid residue(s);

- a pharmaceutical composition comprising such lipoprotein and a phospholipid type of material; and
- a method of facilitating respiration in mammals including man, comprising administering an effective amount of such a lipoprotein or pharmaceutical composition to the respiratory tract of a patient subject to respiratory disorder so as to reduce surface tension at the air-liquid interface of the patient's alveoli.

15 Claims, 3 Drawing Sheets

OTHER PUBLICATIONS

Claypool, W. D., Jr., Chander, A. and Fisher, A. B. (1981) Fed. Proc. 40, 408.

Sueishi, K. and Benson, B. J. (1981) Biochim. Biophys. Acta 665, 442–453.

Suzuki, Y., Nakai, E., Ohkawa, K. (1982) J. Lipid. Res. 23, 53–61.

Suzuki, Y., Curstedt, T., Grossmann, G., Kobayashi, T., Nilsson, R., Nohan K. and Robertson, B. (1986) Eur. J. Respir. Dis. 69, 336–345.

Takahashi, A. and Fujiwara, T. (1980) Biochem. Biophys. Res. Commun. 135, 527–532.

Whitsett, J. A., Hull, W. M., Ohning, G., Ross, G. and Weaver, T. E. (1986) Pediatr. Res. 20, 744–749.

Yu, S.-H. and Possmayer, F. (1986) Biochem. J. 236, 85–89.

Hawgood, S., Benson, B. J., Schilling, J., Damm, D., Clements, J. A. and White, R. T. (1987) Proc. Natl. Acad. Sci. USA 84, 66–70.

Swank, R. T. & Munkres, K. D. (1971) Anal. Biochem. 39, 462–477.

Bartlett, G. R. (1959) J. Biol. Chem. 234, 466–468.

Bizzozero, O., Besio–Moreno, M., Pasquinin, J. M., Soto, E. P. and Gomez, C. J. (182) J. Chromatogr. 227, 33–44.

Hallden, G., Gafvelin, G., Mutt, V. and Jornvall, H. (1986) Arch. Biochem. Biophys. 147, 20–27.

Jornvall, H. and Philipson, L. (1980) Eur. J. Biochem. 104, 237–247.

Fraenkel-Conrat, H. and Tsung, C. M. (1967) in Methods in Enzymology, vol. XI (C. H. W. Hirs, ed.) pp. 151–155.

Bergman, T. and Jornvall, H. (1987) in Methods in Protein Sequence Analysis (K. A. Walsh, et.) Humana Press, Clifton, in Johansson, I., Curstedt, T., Robertsson, B. and Jornvall, H. (1988) Biochemistry 27, 3544–3547.

Enhorning, G. (1977) J. Appl. Physiol. 43, 198–203.

Phospholipids + lipoprotein

Phospholipids only min   max

BIOLOGICALLY ACTIVE LIPOPROTEIN AND ITS USE

The present invention relates to lipoproteins possessing pulmonary surfactant activity, i.e. useful as components of pulmonary surfactant compositions for providing normal respiration in mammals including man. The invention also covers a method of facilitating respiration in mammals including man.

Pulmonary surfactant, which is a phospholipid-protein complex, is essential for normal respiration by reducing surface tension at the air-liquid interface of the alveoli (1). Different surfactant-specific proteins have been detected. One group comprises comparatively large glycoproteins with molecular weights varying between 28 and 36 kDa, depending on the degree of glycosylation (2,3). This protein is soluble in water and the primary structure of the forms from canine and human lung has been determined (4-6). In the presence of calcium ions this protein apparently participates in the formation of surface-active tubular myelin from secreted lamellar bodies (7) and increases the rate of adsorption of surfactant phospholipids (8). Although this protein probably is functional for the endogenous surfactant, synthesized in the alveolar epithelial type II cells, it does not seem to be essential for the physiological activity of exogenous surfactant preparations designed for replacement therapy (9-11).

A second group of surfactant-specific proteins constitutes forms with low-molecular weights ($\leq 14$ kDa) (2,9,12-20). These proteins are very hydrophobic and are composed of different proteins which may be soluble (9) or insoluble (2,16,17) in ether/ethanol.

Both proteins require organic solvents for solubilization and purification, and are heterogenous by multiple start positions in the N-terminal regions (truncated forms). Recombination of either of these proteins with synthetic phospholipids yields a surfactant preparation with physical and biological properties which in many respects are similar to those of natural pulmonary surfactant.

The two low-molecular weight proteins have unrelated structures and sizes; the smaller form is not a fragment of the larger. Recently, cDNA segments of the longer form (21) have been described from dog. The present invention concerns lipophilic low-molecular weight apoproteins of mammalian origin.

Based on extensive scientific research and experimentation and contradictory to previous scientific theories it has now unexpectedly been found, that pulmonary surfactant activity is related to a lipoprotein, wherein an alveloar polypeptide or protein has covalently attached thereto one or two fatty acid residues. The fact that it has turned out that lipoprotein is the active component in compositions possessing pulmonary surfactant activity is an unexpected new discovery, and the scientific theories hitherto launched have all been directed to the belief that the alveolar proteins of relevance are present in admixture with phospholipid type of materials, whereas up to now no one has expected the protein to be covalently associated with any hydrophobic substances, such as fatty acids.

Based on this surprising finding the present invention thus provides a new and novel lipoprotein comprising an alveolar polypeptide or protein and, covalently associated thereto, one or two fatty acid residues.

The fatty acids involved are selected from traditional fatty acids from 14 to 22, such as those having 16 or 18 carbon atoms, and may be selected from palmitic, stearic, oleic, linoleic and linolenic acids. Palmitic and stearic acid residues are preferred, in particular palmitic acid residues. The lipoprotein of this invention preferably contains two palmitic acid residues per polypeptide molecule.

The polypeptide constituting part of the new lipoprotein preferably comprises the minimal amino acid sequence:

Ile-Pro-Cys-Cys-Pro-Val.

This amino acid sequence constitutes the consensus region for all known polypeptides originating from different mammal species.

A preferred polypeptide comprises the amino acid sequence:

```
1                                                    10
Phe—X—Ile—Pro—Cys—Cys—Pro—Val—His—Leu—Lys—Arg.
``` where X is Gly or Arg.

In this sequence X is selected from Gly and Arg, Gly being a preferred amino acid residue.

It is preferred that the polypeptide part of the lipoprotein according to the invention is of human, porcine or bovine origin. In regard to the characterization of such polypeptides reference is made to Feb:s Lett. (1988), Vol. 232, No. 1, 61-64. The full disclosure of this report is incorporated herein by reference.

More specifically, the polypeptide comprises the following amino acid sequence:

```
1            5                            10
Phe—X—Ile—Pro—Cys—Cys—Pro—Val—His—Leu—Lys—Arg—
       15                       20
Leu—Leu—Ile—Val—Val—Val—Val—Val—Val—Leu—Ile—Val—
25                     30                    35
Val—Val—Ile—Val—Gly—Ala—Leu—Leu—Met—Gly—Leu.
```

In this sequence X is again Gly or Arg, preferably the former.

The lipoprotein of the present invention involves polypeptides as outlined above in their N-terminally truncated forms. Such truncation is preferably comprised by one or two amino acid residues.

In regard to the positions of attachment of the fatty acid residues of the polypeptides defined above they are covalently attached to one or both of the cysteine residues in positions 5 and 6 of the molecule, such attachment being such as to form thioesters.

The present invention also involves pharmaceutical compositions comprising in combination a protein or protein composition as defined above and a phospholipid type of material. In such pharmaceutical composition the protein is a minor component, and a preferred weight range of the contents of the composition of the protein is about 0.5 to about 10% by weight thereof. It is particularly preferred that the protein constitutes about 1 to 5% by weight of the composition as a whole. As an example of phospholipid material there may be mentioned phospholipids based on palmitic acid. In addition to such phospholipid matrix the composition of the invention may also contain other additives, such as pharmaceutically acceptable carriers or diluents, stabilising agents, and other conventionally used pharmaceutically acceptable additives.

The lipoproteins according to the present invention have been found to contribute significantly to pulmonary surfactant activity. Accordingly, the lipoproteins and compositions of the invention are particularly useful as components of pulmonary surfactants. Furthermore, the invention includes a method for facilitating respiration in mammals including man, such method comprising administering an effective amount of a lipoprotein or composition according to the invention to the respiratory tract of a patient in need of treatment for respiratory disorders. By such administration it is possible to significantly reduce surface tension at the air-liquid interface of the patient's alveoli. The administration can take place directly into trachea or bronchi, but can also take place through the oral cavity by using an aerosol spray of a conventional type.

In the following the present invention will be further illustrated by non-limiting examples. This exemplification will be made with reference to the appended drawings, wherein FIG. 1 shows the mass spectrogram of human surfactant lipoprotein;

Figure 1:
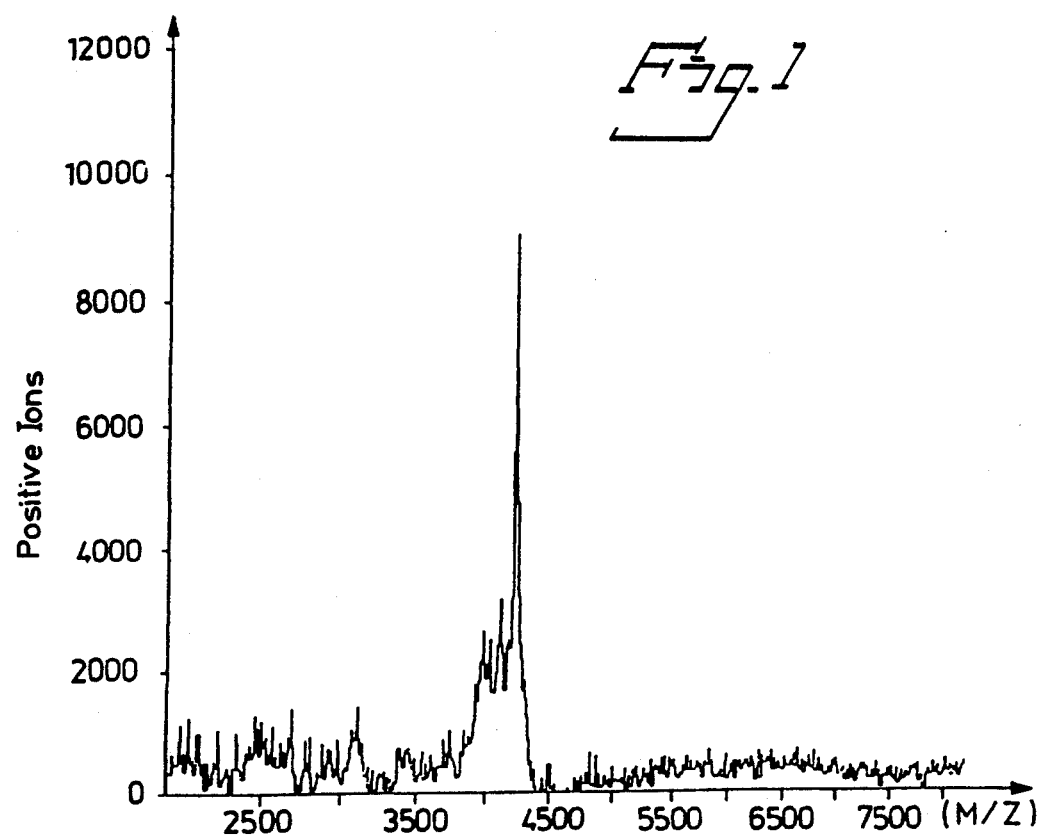

The lipoproteins according to this invention are highly hydrophobic and require organic solvents for solubilization and purification.

EXAMPLE 1

Isolation of human low molecular weight surfactant protein.

Bronchoalveolar lavage

Bronchoalveolar lavage (BAL) on humans was carried out with a flexible bronchoscope under local anesthesia. The bronchoscope was wedged in a middle lobe bronchus and sterile saline solution at 37° C. was instilled in aliquots of 50 ml. The total volume instilled varied between 200 and 300 ml. The fluid was gently suctioned back after each instillation and collected in a siliconized bottle kept on ice. Immediately after completion of the lavate the bottle was transported to the laboratory.

The recovered BAL fluid was strained through a double layer of Dacron nets and the volume was measured. It was centrifuged at 400 g at 4° C. for 5 min and the supernatant was stored at −20° C. until further analyzed.

Amniotic fluid.

Human amniotic fluid, obtained from full term pregnancies at Caesarian sections and vaginal deliveries, was filtered through a net and the volume was measured and the material was stored at −20° C. until further analyzed.

Isolation of hydrophobic proteins from bronchoalveolar and amniotic fluids.

To 300 ml of amniotic or BAL fluids 400 ml of methanol was added and the solution was mixed by shaking and ultrasonication. 800 ml of chloroform was added and the mixture was shaken. After filtration the lower phase was evaporated to dryness and the phospholipid fraction which also contains the hydrophobic proteins was isolated by reverse phase chromatograph on Lipidex-5000 in a system of ethylene chloride/methanol 1:4 (v/v).

EXAMPLE 2

Analysis of surfactant lipoproteins.

For determination of amino acid compositions, the proteins were reduced with dithioerythritol (about 30 nmol/nmol peptide; 37° C.; 2 h) and carboxymethylated by addition of neutralized iodo ($^{14}$C) acetate (120 nmol/nmol peptide; 37° C.; 2 h) in 8M urea, 0.4M Tris/HCX1, 2 mM EDTA. Excess reagents were removed by exclusion chromatography on Sephadex LH-60 (40×1.1 cm) in chloroform/methanol 1:1 (v/v) containing 5% 0.1M HCl. For analysis of amino acid compositions, samples were hydrolyzed in evacuated tubes for 24 h at 110° C. and for 72 and 120 hrs, respectively, at 150° C., with 6M HCl containing 0.5% phenol. Total amino acid composition of human surfactant lipoprotein is illustrated in Table 1. Liberated amino acids were analyzed with a Beckman 120M instrument.

The apparent molecular weight was determined by SDS/polyacrylamide gel electrophoresis (using a 10% gel containing 8M urea)(22). Molecular weight markers were purchased from BDH Chemicals Ltd (England) and consisted of horse-heart myoglobin, cleaved by cyanogen bromide. Phosphorus was analyzed according to Bartlett (23).

Preparations for sequence analysis were applied in chloroform/methanol 1:2.

Structural analysis

The lipoprotein fractions were reduced by treatment with dithiothreitol (30 nmol/nmol polypeptide) at 37° C. for 2 h, under nitrogen. The reduced samples were then $^{14}$C-carboxymethylated by treatment with neutralized iodo ($^{14}$C)-acetic acid (120 nmol/nmol polypeptide; 37° C.; 2 h) and purified by exclusion chromatography on Sephadex LH-60.

Samples for sequence analysis of the $^{14}$C-carboxymethylated protein were removed after solubilization in chloroform/methanol. Samples for cleavages with pepsin were dissolved in 100% formic acid, diluted to 5% formic acid, and then submitted to the enzyme (1:30, enzyme to substrate ratio; 37° C.; 2 h). The peptic peptides were separated by high-performance liquid chromatography on an Ultropac C-18 column in 0.1% trifluoroacetic acid with a linear gradient of acetonitrile. Samples for treatment with CNBr were dissolved in 100% formic acid, diluted to 70%, and then treated with CNBr (0.1 g/ml) at room temperature for 24 h. CNBr fragments were separated on Sephadex LH-60 in chloroform/methanol, 1:1 (v/v) containing 5% 0.1M HCl (24).

Gas-phase sequencer analysis was performed by degradation in an Applied Biosystems 470 A instrument and phenylthiohydantoin detection by reverse-phase high performance liquid chromatography using a Hewlett Packard 1090 instrument (25). Samples for liquid-phase sequencer analysis in a Beckman 890C instrument were applied to glycine-precycled Polybrene (26), and analyzed by a similar high performance liquid chromatography system. Total compositions were obtained by hydrolysis with 6M HCl/0.5% phenol at 100° C. for 24 h in vacuum. Hydrazinolysis was performed with anhydrous hydrazine in 100° C. for 6 h in evacuated tubes (27). Amino acids were quantitated with a ninhydrin-based Beckman 121M amino acid analyzer, or with a phenylthiocarbamyl-based high performance liquid chromatography system (28). N-terminal truncation of the surfactant proteins is illustrated in Table 2.

The molecular weight of the surfactant lipoprotein was determined by "Time of flight" mass spectroscopy (Bioion, Uppsala, Sweden) using an acceleration voltage of 18 000 volts. Bovine insulin was used as an internal reference standard.

The lipoprotein was reduced with dithioerythritol (about 30 mol/mol peptide; 37° C.; 2 h) and analyzed by mass spectrometry. The nonreduced and reduced material had similar molecular weights, about 480 mass units greater than what would be anticipated from the weight of the 35 amino acids (FIG. 1). To investigate the hypothesis that native surfactant lipoprotein consists of fatty acids covalently linked to the peptide sequence to yield a proteolipid, the nonreduced lipoprotein was dissolved in chloroform/methanol 1:2 (v/v) and aq. 2M Trimethylamine was added to a final concentration of 200 mM.

The mixture was incubated for 4 h at 37° C. Fatty acids were released and separated from the polypeptide by exclusion chromatography on Sephadex LH-60 in chloroform/methanol 1:1 (v/v) containing 5% 0.1 M HCl. Fatty acids, mainly palmitic acid, were recovered.

Figure 2:
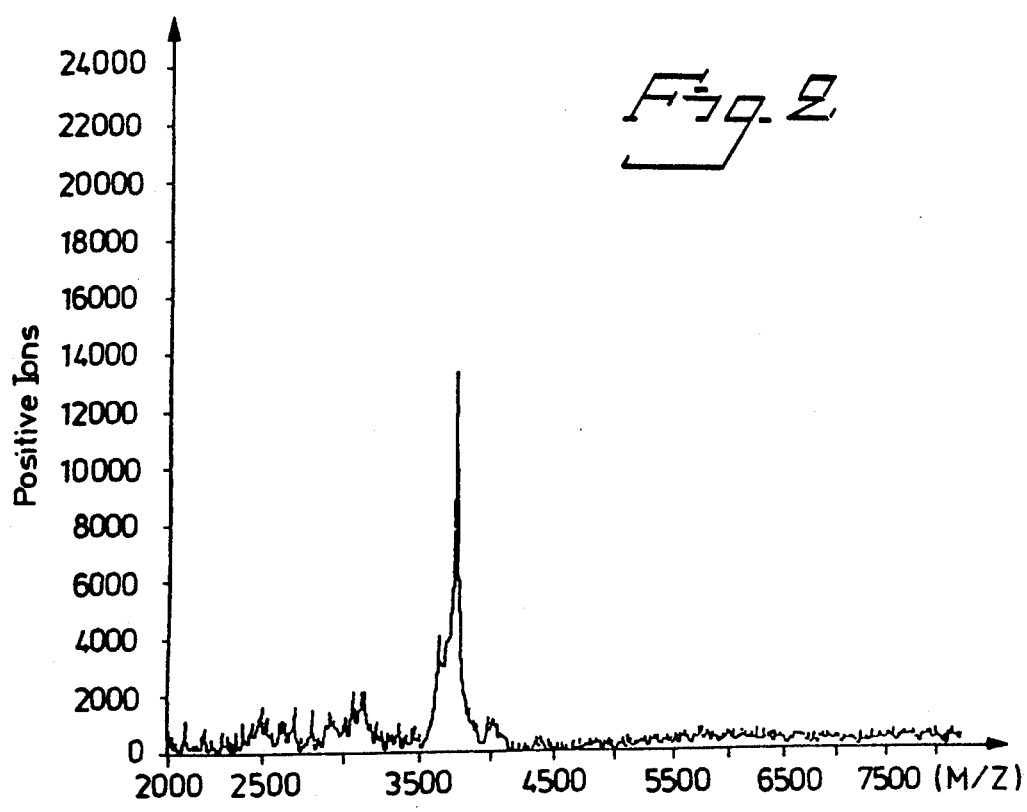
FIG. 2 shows the corresponding mass spectrogram after treatment with trimehyl amine.

When the peptide fraction obtained was analyzed by "Time of flight" mass spectrometry (FIG. 2) it was evident that the molecular weight had decreased by about 478 mass units upon trimethylamine treatment.

This reduction in molecular weight corresponds to the loss of two palmitic acid residues probably esterified to the sulfhydryl groups of Cys 5 and Cys 6.

To confirm that the trimethylamine treatment that released to palmitic acid residues from the surfactant peptide also generated free thiol groups, the following experiment was made:

Separate samples of the native surfactant lipoprotein were treated with trimethylamine and any liberated thiol groups were then carboxymethylated by treatment with dithioerythritol, to prevent reoxidation, followed by iodoacetate.

Figure 3:
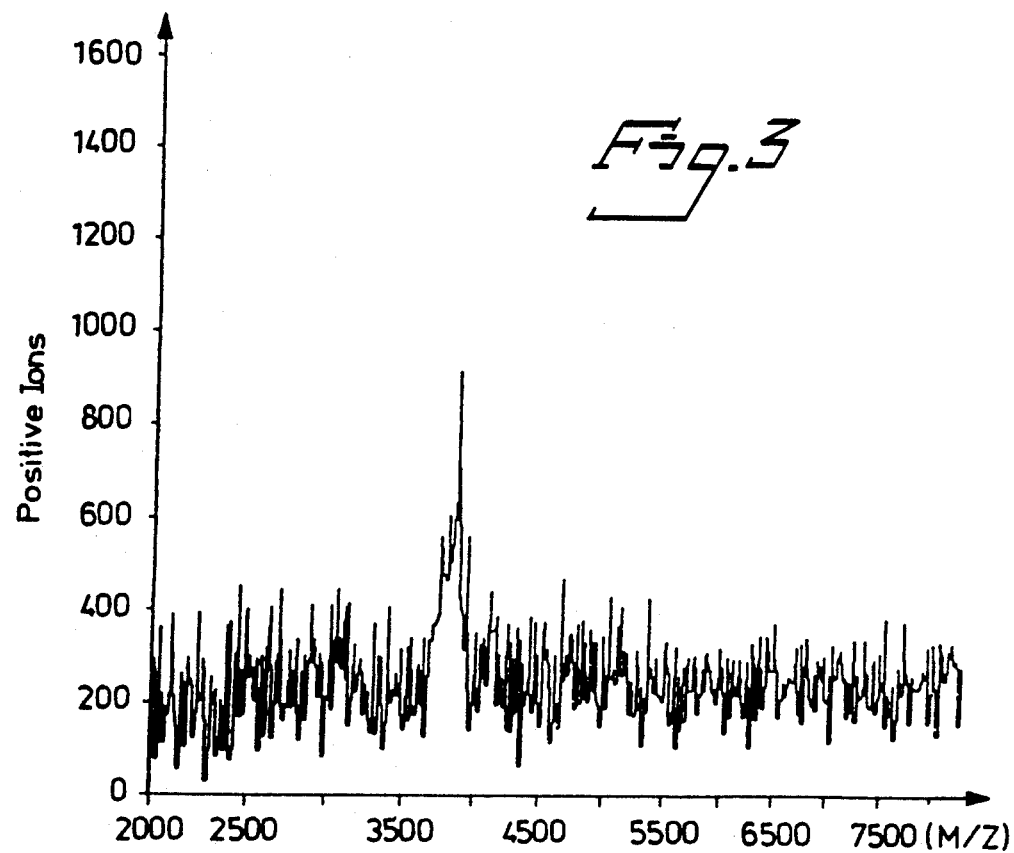
FIG. 3 shows the corresponding mass spectogram after treatment with trimethyl amine followed by iodoacetate.

Mass spectroscopical analysis (FIG. 3) demonstrates a gain of about 120 mass units compared to the trimethylamine treated peptide fraction. An increase in molecular weight of 120 agrees well with carboxymethylation of the thiol groups of Cys 5 and Cys 6.

As a further demonstration of the presence of two esterified palmitic acid residues the native lipoprotein was treated with 0.01M KOH in methanol/water 98:2 (v/v) at +37° C. for 30 min. The peptide was recovered from the unpolar phase (29).

Figure 4:
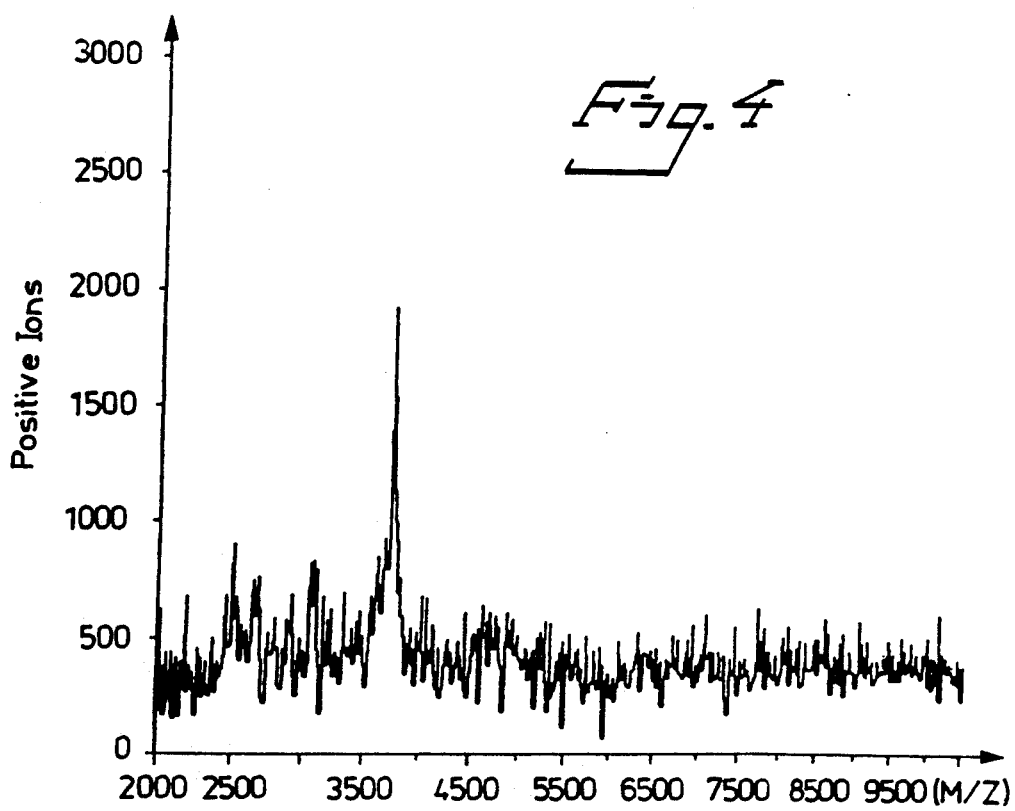
FIG. 4 shows the mass spectrogram after treatment with potassium hydroxide.

Analysis of this peptide material by "Time of flight" mass spectroscopy (FIG. 4) again shows a reduction in molecular weight of about 480 mass units compared to the native sufactant peptide, demonstrating the loss of two covalently conjugated palmitic acid residues after alkaline hydrolysis.

In FIG. 1 two smaller peaks can be distinguished. One at position −240 relative to the main peak probably represents a small proportion of the peptide material esterified with palmitic acid at only one of the two crysteine residues.

Taken together these data clearly indicate that at least one but preferentially two palmitic acid residues are covalently conjugated to the peptide by esterification to the thiol groups of Cys 5 and Cys 6.

EXAMPLE 3

Recombination of isolated lipoprotein fractions with synthetic phospholipids.

1.2-Dipalmitoyl-sn-glycero-3-phosphocholine (DPPC), 1-palmitoyl-2-oleoyl-sn-glycero-3-phosphocholine (POPC) and 1,2-dipalmitoyl-sn-glycero-3-phosphoglycerol (DPPG) were purchased from Sigma Chemical Co. (St. Louis, MO), and were used without further purification. The phospholipids were dissolved in chloroform/methanol 2:1 (v/v) mixed in the proportions DPPC:POPC:DPPG 55:35:10 (w/w/w) and used as the surfactant preparation "phospholipids".

To this mixture surfactant lipoprotein dissolved in chloroform/methanol 1:2 (v/v) was added, giving a lipoprotein to phospholipid ratio of 1:50. The solvents were evaporated to dryness and the different surfactant preparations (phospholipids, phospholipids+lipoprotein fraction) were suspended in saline giving a phospholipid concentration of 10 or 80 mg/ml.

EXAMPLE 4

Determination of in-vitro surface properties.

The surface properties of the lipoprotein-based artificial surfactant were analyzed with a pulsating bubble instrument (Surfactometer International, Toronto, Canada) (30). The surfactant preparations were suspended at a phospholipid concentration of 10 mg/ml, and the pressure gradient across the bubble wall was recorded at 37° C. during 50% cyclic surface compression at the rate of 40/min. Surface tension was assessed at maximal and minimal bubble sizes during the 5th cycle and after 1 and 5 min of pulsation.

Figure 5:
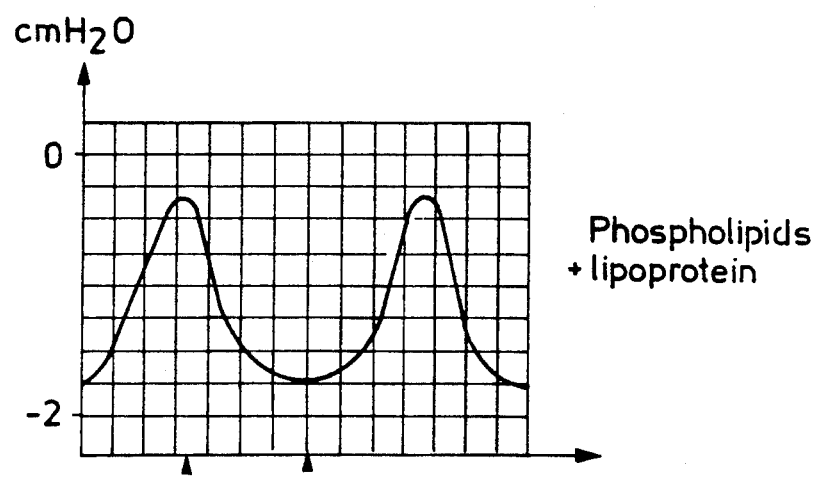
FIG. 5 shows diagrams on surface activity of artificial surfactant preparations using the pulsating bubble technique.
Figure 5:
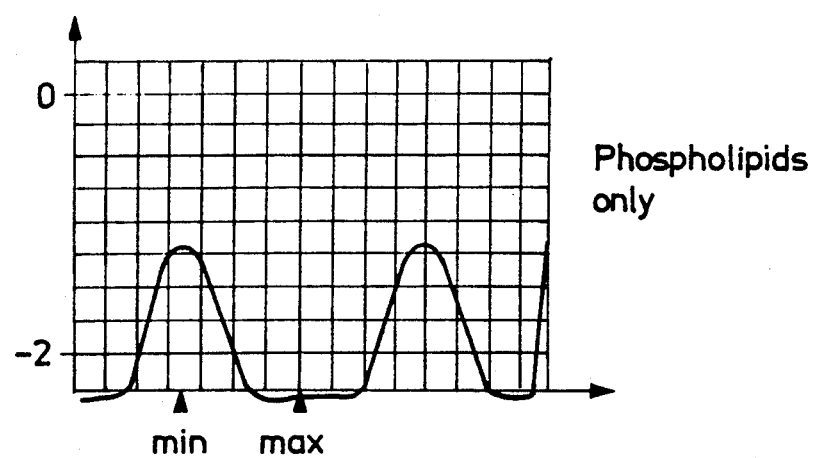

The results of these experiments are shown in FIG. 5. The tracings therein represent pressure gradients across the bubble wall; max and min indicate maximal (radius 0.55 mm) and minimal (radius 0.40 mm) bubble size during pulsation at a rate of 40/min. A pressure gradient close to zero at minimal bubble size corresponds to nearly zero surface tension.

EXAMPLE 5

Effect of removal of the fatty acid residues on in vitro surfactant properties.

Native or trimethylamine-treated lipoprotein was mixed with protein-free phospholipids, obtained from lung surfactant by chromatography on Sephadex LH-60. These artificial surfactant preparations, containing 0-4% of lipoprotein or the protein fraction obtained by the treatment were suspended in saline at a phospholipid concentration of 10 mg/ml and analyzed with a pulsating bubble instrument. The pressure gradient across the bubble wall was recorded at 37° C. during 50% cyclic surface compression at the rate of 40/min. Surface tension at maximal and minimal bubble sizes was determined during the 5th, 40th and 200th cycle of pulsation. The surface adsorption rate was then determined by arresting the pulsation at maximal bubble size and recording the time interval until static surface tension had dropped to the level of 30 mN/m.

The surfactant preparation containing 2% of the native lipoprotein had a rapid adsorption (<2 s) and a minimum surface tension near 0 mN/m. The corresponding mixture with trimethylamine treated lipoprotein had slow adsorption (>120 s) and a high minimum surface tension (about 20 mN/m). Thus, acyl residues covalently bound to the polypeptide are essential for the physiological activity of the surfactant.

EXAMPLE 6

Preparation of synthetic peptides.
The peptides $$
\begin{array}{c}
10\\
H_2N-Phe-Arg-Ile-Pro-Cys-Cys-Pro-Val-His-Leu-Lys-Arg-COOH\\
10\\
H_2N-Phe-Arg-Ile-Pro-Cys-Cys-Pro-Val-His-Leu-Lys-Arg-Leu-Leu-Ile-Val-Val-COOH\\
H_2N-Ile-Pro-Cys-Cys-Pro-Val-COOH
\end{array}
$$

were synthesized according to the stepwise solid phase technique in an Applied Biosystems Model 430A peptide synthesizer. A phenylacetamidomethyl (PAM) resin was used as the solid support and the following tert-butyloxycarbonyl (t-Boc) amino acid derivatives were employed:L-Arg-Tosyl, LCys-4-Methyl-Benzyl, L-Lys-Cl-Benzyloxycarbonyl, L-Asn, L-Pro, L-Ala, L-Val, L-Met, L-Ile, L-Leu and Gly. A standard program including pre-formation of symmetric anhydrides was used for the synthesis. The resulting peptides were cleaved from the resin and deprotected by the hydrogen fluoride (HF) method and subsequently purified by reverse phase high performance liquid chromatography (HPLC). The identity and purity of the final product was assessed by amino acid hydrolysis. (31) Kent, S.B.H. (1980) Ann. Rev. Biochem. 57, 957–989.

EXAMPLE 7

Preparation of thioester lipopeptide.
The conjugation of redestillation Palmitoyl-chloride (Fluka) and the hexapeptide H$_2$N-Ile-Pro-Cys-Cys-Pro-Val-COOH was performed as follows:

3 mg (4.8 μmol) of the hexapeptide was dissolved in 500 μl of chloroform/methanol 1:2 (v/v).

25 μl of 0.5M DTE (12.5 μmol) was added to the solution. The mixture was flushed with N$_2$ and incubated 160 minutes in 37° C.

20 μl of 3.3M Palmitoyl-chloride (66 μmol) was added, the mixture flushed with N$_2$ and incubated 250 minutes in 37° C.

The acylated peptide was isolated by TLC and its MW was confirmed.

When tested in accordance with the procedure described in Example 4 the lipopeptide performs similarly as the native lipoprotein.

EXAMPLE 8

Determination of in-vitro surface properties of artificial surfactants consisting of synthetic phospholipids and synthesized SP-C polypeptide (without thioester bound palmitic acid).

The SP-C polypeptide was synthesized according to the stepwise solid phase technique in an Applied Biosystems Model 430A peptide synthesizer. A phenylacetamidomethyl resin was used as the solid support and the polypeptide was cleaved from the resin and deprotected by the hydrogen fluoride method. The polypeptide was extracted from the resin with chloroform/methanol 1:1 (v/v) with and without 5% 0.1M HCl present, yielding about 30% of the sample. The material was dissolved in a small amount of concentrated formic acid, diluted with chloroform/methanol 1:1 (v/v) and purified by Sephadex LH-60 chromatography in chloroform/methanol 1:1 (v/v) containing 5% formic acid. The identity and purity of the final product were assessed by amino acid hydrolysis, sequencer degradation and time-of-flight mass spectrometry.

Various amounts of the purified synthesized polypeptide SP-C were recombined with the synthetic phospholipid mixture used in Example 3. The phospholipids were dissolved in chloroform/methanol 2:1 (v/v), mixed in the proportions DPPC:POPC:DPPG 55:35:10 (w/w/w) and used as the surfactant preparation "phospholipids".

Various amounts of synthetic SP-C polypeptide, dissolved in formic acid, was added to different tubes and the acid was evaporated to dryness. After addition of the phospholipids, the organic solvents were evaporated to dryness and the different surfactant preparations were suspended in saline at a phospholipid concentration of 10 mg/ml. These artificial surfactant preparations, containing 0–20% of synthetic SP-C polypeptide, were analyzed with a pulsating bubble instrument. The pressure gradient across the bubble wall was recorded at 37° C. during 50% cyclic surface compression at the rate of 40/min. Surface tension at maximal and minimal bubble size was determined during the 5th, 40th and 200th cycle of pulsation. The surface adsorption rate was then determined by arresting the pulsation at maximal bubble size and recording the time interval until static surface tension had dropped to the level of 30 mN/m. All preparations had very slow adsorption (>120 s) and high minimum (>20 mN/m) and maximum (>44 mN/m) surface tension (Table 3). The results show that the SP-C polypeptide (without palmitoyl residues) has no effect on surface activity. The slow adsorption and high surface tension values preclude the use of these preparations for treatment of infants.

EXAMPLE 9

Determination of in-vitro surface properties of artificial surfactants consisting of synthetic phospholipids and native or trimethylamine-treated (=deacylated) SP-C.

The molecular weight of native and trimethylamine-treated SP-C was determined by time-of-flight mass spectrometry. The mass spectrum showed that native SP-C contained mainly two palmitoyl residues and small amounts of molecules with one palmitoyl residue. The trimethylaminetreated SP-C was purified on Sephadex LH-60 in chloroform/methanol 1:1 (v/v), containing 5% 0.1M HCl and analyzed by time-of-flight mass spectrometry. This trimethylamine-treated SP-C was completely deacylated. Various amounts of native or deacylated SP-C was recombined with the synthetic phospholipid mixture used in Example 3. The phospholipids were dissolved in chloroform/methanol 2:1 (v/v), mixed in the proportions DPPC:POPC:DPPG 55:35:10 (w/w/w) and used as the surfactant preparation "phospholipids".

To these phospholipid mixture various amounts of native or deacylated SP-C, dissolved in chloroform-/methanol 1:2 (v/v), were added. The organic solvents were evaporated to dryness and the different surfactant preparations were suspended in saline at a phospholipid concentration of 10 mg/ml. These artificial surfactant preparations, containing 0-4% of native or deacylated SP-C, were analyzed with a pulsating bubble instrument. The pressure gradient across the bubble wall was recorded at 37° C. during 50% cyclic surface compression at the rate of 40/min. Surface tension at maximal and minimal bubble size was determined during the 5th, 40th and 200th cycle of pulsation. The surface adsorption rate was then determined by arresting the pulsation at maximal bubble size and recording the time interval until static surface tension had dropped to the level of 30 mN/m. The results show that preparations containing native SP-C increased the in-vitro surface activity. Thus, a concentration of 2% of native SP-C in the preparation gave a rather rapid adsorption (16 s), a minimum surface tension near 0 mN/m and a maximum surface tension about 30 mN/m (Table 4). These results are similar to the in-vitro surface activity of natural porcine surfactant preparations (adsorption <1 s, minimum and maximum surface tension during the 200th cycle <3 mN/m and 30 mN/m, respectively) successfully used for treatment of infants. The adsorption time is somewhat longer than that obtained with natural surfactant due to the more complex and unsaturated phospholipid mixture in the natural surfactant. Addition of deacylated SP-C to the phospholipid mixture did not improve the surface properties. All preparations had very slow adsorption (>120 s) and high minimum ($\geq$18 mN/m) and maximum ($\geq$50 mN/m) surface tension (Table 5). The results indicate that the surfactant preparations containing deacylated SP-C would be ineffective for treatment of infants.

REFERENCES

1. Goerke, J. (1974) Biochim. Biophys. Acta 374, 241-261.
2. King, R. J., Klass, D. J., Gikas, E. G. and Clements, J. A. (1973) Am.J.Physiol. 224., 788-795.
3. van Golde, L. M. G., Batenburg, J. J. and Robertson, B. (1987) Physiol.Rev., in press.
4. Benson, B., Hawgood, S., Shilling, J., Clements, J., Damm, D., Cordell, B. and White, R. T. (1985) Proc.Natl.Acad.Sci.USA 82, 6379-6383.
5. White, R. T., Damm, D., Miller, J., Spratt, K., Shilling, J., Hawgood, S., Benson, B. and Cordell, B. (1985) Nature 317, 361-363.
6. Floros, I., Steinbrink, R., Jacobs, K., Phelps, D., Kriz, R., Recny, M., Sultzmann, L., Jones, S., Taeusch, H. W., Frank, H. A. and Fritsch, E. F. (1986) J.Biol.Chem. 261, 9029-9033.
7. Benson, B. J., Williams, M. S., Sueishi, K., Goerke, J. and Sargeant, T. (1984) Biochim.Biophys.Acta 793, 18-27.
8. King, R. J. and MacBeth, M. C. (1979) Biochim.Biophys.Acta 557, 86-101.
9. Whitsett, J. A., Ohning, B. L., Ross, G., Meuth, J., Weaver, T., Holm, B. A., Shapiro, D. L. and Notter, R. H. (1986) Pediatr. Res. 20, 460-467.
10. Metcalfe, I. L., Enhorning, G. and Possmayer, F. (1980) J.Appl.Physiol. 49, 34-41.
11. Berggren, P., Curstedt, T., Grossman, G., Nilsson, R. and Robertson, B. (1985) Exp. Lung Res. 8, 29-51.
12. Phizackerley, P. J. R., Town, M.-H. and Newman, G. E. (1979) Biochem.J. 183, 731-736.
13. Katyal, S. L. and Singh, G. (1979) Lab. Invest. 40, 562-567.
14. Claypool, W. D., Jr., Chander, A. and Fisher, A. B. (1981) Fed.Proc. 40, 408.
15. Sueishi, K. and Benson, B. J. (1981) Biochim.Biophys.Acta 665, 442-453.
16. Suzuki, Y., Nakai, E., Ohkawa, K. (1982) J.Lipid.Res. 23, 53-61.
17. Suzuki, Y., Curstedt, T., Grossmann, G., Kobayashi, T., Nilsson, R., Nohan, K. and Robertson, B. (1986) Eur.J.Respir.Dis. 69, 336-345.
18. Takahashi, A. and Fujiwara, T. (1980) Biochem.Biophys.Res.Commun. 135, 527-532.
19. Whitsett, J. A., Hull, W. M., Ohning, G., Ross, G. and Weaver, T. E. (1986) Pediatr.Res.20, 744-749.
20. Yu, S.-H. and Possmayer, F. (1986) Biochem.J. 236, 85-89.
21. Hawgood, S., Benson, B. J., Schilling, J., Damm, D., Clements, J. A. and White, R. T. (1987) Proc.Natl.Acad.Sci.USA 84, 66-70.
22. Swank, R. T. & Munkres, K. D. (1971) Anal.Biochem. 39, 462-477.
23. Bartlett, G. R. (1959) J.Biol.Chem. 234, 466-468.
24. Bizzozero, O., Besio-Moreno, M., Pasquini, J. M., Soto, E. P. and Gomez, C. J. (1982) J.Chromatogr. 227, 33-44.
25. Hallden, G., Gafvelin, G., Mutt, V. and Jörnvall, H. (1986) Arch.Biochem.Biophys. 147, 20-27.
26. Jörnvall, H. and Philipson, L. (1980) Eur.J.Biochem. 104, 237-247.
27. Fraenkel-Conrat, H. and Tsung, C. M. (1967) in Methods in Enzymology, vol. XI (C. H. W.Hirs, ed.) pp. 151-155.
28. Bergman, T. and Jörnvall, H. (1987) in Methods in Protein Sequence Analysis (K. A. Walsh, ed.) Humana Press, Clifton, in
29. Johansson, I., Curstedt, T. Robertsson, B. and Jörnvall, H. (1988) Biochemistry 27, 3544-3547.
30. Enhorning, G. (1977) J.Appl.Physiol.43, 198-203.

TABLE 1

| | Human surfactant lipoprotein | | | | |
|---|---|---|---|---|---|
| | 110° C. | | | 150° C. | |
| | 24h | 72h | 168h | 24h | 72h |
| Cys (Cm) | 0.7 (2) | | | | |
| Pro | 2.5 (3) | | | | |
| Gly | 3.0 (2) | | | | |
| Ala | 1.4 (1) | | | | |
| Val | 2.4 (10) | 2.5 (10) | 2.8 (10) | 8.0 (10) | 8.6 (10) |
| Met | 1.0 (1) | | | | |
| Ile | 1.2 (3) | 1.3 (3) | 1.4 (3) | 2.2 (3) | 1.4 (3) |
| Leu | 5.1 (7) | 5.1 (7) | 4.7 (7) | 6.2 (7) | 7.8 (7) |
| Phe | 0.8 (1) | | | | |
| Lys | 1.2 (1) | | | | |
| His | 0.8 (1) | | | | |
| Arg | 1.2 (2) | | | | |
| Trp | n.d. (1) | | | | |

TABLE 2

| Hum lipoprotein | Phe-Gly/Arg-Ile-Pro- | 32% | 55% |
|---|---|---|---|
| | Gly/Arg-Ile-Pro- | 36% | 19% |
| | Ile-Pro- | 32% | 26% |
| | A | B | |

A: Amniotic fluid
B: Bronchoalveolar lavage

TABLE 3

Surface properties (median values) of synthetic phospholipids (10 mg/ml) recombined with different amounts of synthetic SP-C polypeptide.
The recordings were obtained with a pulsating bubble at 37° C., 50% surface compression and rate 40/min. Five experiments were performed for each preparation.

| SP-C POLY-PEPTIDE (%) | ADSORP-TION (s) | SURFACE TENSION (mN/m) | | | | | |
|---|---|---|---|---|---|---|---|
| | | 5th cycle | | 40th cycle | | 200th cycle | |
| | | $\tau_{min}$ | $\tau_{max}$ | $\tau_{min}$ | $\tau_{max}$ | $\tau_{min}$ | $\tau_{max}$ |
| 0 | >120 | 20 | 52 | 20 | 55 | 22 | 58 |
| 1.0 | >120 | 32 | 65 | 29 | 63 | 22 | 58 |
| 2.0 | >120 | 27 | 61 | 24 | 58 | 20 | 56 |
| 4.0 | >120 | 27 | 51 | 24 | 50 | 21 | 49 |
| 10 | >120 | 30 | 51 | 29 | 50 | 26 | 50 |
| 20 | >120 | 36 | 47 | 35 | 45 | 34 | 44 |

TABLE 4

Surface properties (median values) of synthetic phospholipids (10 mg/ml) recombined with different amounts of native SP-C.
The recordings were obtained with a pulsating bubble at 37° C., 50% surface compression and rate 40/min. Five experiments were performed for each preparation.

| NATIVE SP-C (%) | ADSORP-TION (s) | SURFACE TENSION (mN/m) | | | | | |
|---|---|---|---|---|---|---|---|
| | | 5th cycle | | 40th cycle | | 200th cycle | |
| | | $\tau_{min}$ | $\tau_{max}$ | $\tau_{min}$ | $\tau_{max}$ | $\tau_{min}$ | $\tau_{max}$ |
| 0 | >120 | 22 | 60 | 22 | 58 | 21 | 54 |
| 1.0 | 88 | 12 | 41 | 12 | 38 | 11 | 52 |
| 2.0 | 16 | 13 | 33 | 11 | 30 | 1 | 32 |
| 4.0 | 26 | 12 | 41 | 6 | 39 | 1 | 35 |

TABLE 5

Surface properties (median values) of synthetic phospholipids (10 mg/ml) recombined with different amounts of deacylated SP-C.
The recordings were obtained with a pulsating bubble at 37° C., 50% surface compression and rate 40/min. Five experiments were performed for each preparation.

| DEACY-LATED SP-C (%) | ADSORP-TION (s) | SURFACE TENSION (mN/m) | | | | | |
|---|---|---|---|---|---|---|---|
| | | 5th cycle | | 40th cycle | | 200th cycle | |
| | | $\tau_{min}$ | $\tau_{max}$ | $\tau_{min}$ | $\tau_{max}$ | $\tau_{min}$ | $\tau_{max}$ |
| 0 | >120 | 25 | 56 | 27 | 54 | 23 | 53 |
| 1.0 | >120 | 19 | 55 | 22 | 56 | 18 | 56 |
| 2.0 | >120 | 21 | 54 | 22 | 54 | 21 | 54 |
| 4.0 | >120 | 39 | 52 | 37 | 50 | 27 | 50 |

We claim:

1. A purified lipoprotein possessing pulmonary surfactant activity comprising an alveolar polypeptide or protein of human origin including the amino acid sequence:

$$\text{Phe}-\text{Gly}-\text{Ile}-\text{Pro}-\text{Cys}-\text{Cys}-\text{Pro}-\text{Val}-\text{His}-\text{Leu}-\text{Lys}-$$
(1 to 10)

$$\text{Arg}-\text{Leu}-\text{Leu}-\text{Ile}-\text{Val}-\text{Val}-\text{Val}-\text{Val}-\text{Val}-\text{Val}-$$
(15 to 20)

$$\text{Leu}-\text{Ile}-\text{Val}-\text{Val}-\text{Val}-\text{Ile}-\text{Val}-\text{Gly}-\text{Ala}-\text{Leu}-\text{Leu}-$$
(25 to 30)

$$\text{Met}-\text{Gly}-\text{Leu}$$

and, covalently bound thereto, one or two fatty acid residue(s).

2. A lipoprotein according to claim 1, wherein said fatty acid residue is selected from the group consisting of residues of fatty acids having from 14 to 22 carbon atoms.

3. A lipoprotein according to claim 2, wherein said acids are selected from the group consisting of palmitic, stearic, oleic, linoleic and linolenic acids.

4. A lipoprotein according to claim 3, wherein said acids are saturated.

5. A lipoprotein according to claim 4, wherein said acids are selected from the group consisting of palmitic and stearic acids.

6. A lipoprotein according to claim 4, wherein said fatty acid residue is a palmitic acid residue.

7. A lipoprotein according to claim 1 containing two fatty acid residues.

8. A lipoprotein according to claim 1, wherein said polypeptide is in an N-terminal truncated form, the truncation comprising 1 or 2 amino acid residues.

9. A lipoprotein according to claim 1, wherein said fatty acid residue(s) is (are) covalently attached to one (or both) of the Cys residues to form thioesters therewith.

10. A lipoprotein according to claim 9, wherein the number of fatty acid residues is two (2).

11. A lipoprotein according to claim 9, wherein said fatty acid residue is a palmitic acid residue.

12. A pharmaceutical composition comprising in combination a lipoprotein according to claim 1 and a phospholipid type of material.

13. A method of facilitating respiration in mammals including man, comprising administering an effective amount of a lipoprotein or pharmaceutical composition thereof according to claim 1, to the respiratory tract of a patient subject to respiratory disorder so as to reduce surface tension at the air-liquid interface of the patient's alveoli.

14. A method according to claim 13, wherein the administration is performed directly into the trachea or bronchii.

15. A lipoprotein according to claim 10, wherein said fatty acid residue is a palmitic acid residue.

* * * * *